(12) United States Patent
Cosmescu

(10) Patent No.: US 11,291,491 B2
(45) Date of Patent: Apr. 5, 2022

(54) ELECTROSURGERY BLADE AND ELECTROSURGERY BLADE ASSEMBLY

(71) Applicant: I.C. Medical, Inc., Phoenix, AZ (US)

(72) Inventor: Ioan Cosmescu, Phoenix, AZ (US)

(73) Assignee: I.C. Medical, Inc., Phoenix, AZ (US)

( * ) Notice: Subject to any disclaimer, the term of this patent is extended or adjusted under 35 U.S.C. 154(b) by 1153 days.

(21) Appl. No.: 15/147,730

(22) Filed: May 5, 2016

(65) Prior Publication Data
US 2017/0319255 A1    Nov. 9, 2017

(51) Int. Cl.
| | | |
|---|---|---|
| A61B 18/14 | (2006.01) | |
| A61B 18/04 | (2006.01) | |
| A61B 18/12 | (2006.01) | |
| A61B 18/00 | (2006.01) | |

(52) U.S. Cl.
CPC ............ *A61B 18/042* (2013.01); *A61B 18/12* (2013.01); *A61B 18/1402* (2013.01); *A61B 2018/00577* (2013.01); *A61B 2018/1412* (2013.01)

(58) Field of Classification Search
CPC ... A61B 18/042; A61B 18/12; A61B 18/1402; A61B 2018/00577; A61B 2018/1412; A61B 2218/001; A61B 2218/005; A61B 2218/006

See application file for complete search history.

(56) References Cited

U.S. PATENT DOCUMENTS

| | | | | |
|---|---|---|---|---|
| 4,232,676 | A * | 11/1980 | Herczog | A61B 18/14 606/48 |
| 4,589,411 | A * | 5/1986 | Friedman | A61B 18/10 331/127 |
| 4,674,498 | A * | 6/1987 | Stasz | A61B 18/1402 604/22 |
| 4,850,353 | A | 7/1989 | Stasz et al. | |
| 4,862,890 | A * | 9/1989 | Stasz | A61B 18/1402 606/48 |
| 5,154,709 | A * | 10/1992 | Johnson | A61B 18/1402 604/35 |
| 5,171,311 | A | 12/1992 | Rydell et al. | |
| 5,241,990 | A * | 9/1993 | Cook | A61M 1/0062 137/625.46 |

(Continued)

OTHER PUBLICATIONS

International Search Report and the Written Opinion of the International Searching Authority from related PCT Application No. PCT/US2017/031137 dated Jul. 25, 2017.

*Primary Examiner* — Jaymi E Della
*Assistant Examiner* — Sean W Collins
(74) *Attorney, Agent, or Firm* — Zeman-Mullen & Ford, LLP

(57) ABSTRACT

Electrosurgery blades including electrosurgery blade assemblies having argon beam capability. The electrosurgery blade includes a non-conductive planar member having opposite planar sides and a sharp cutting tip and a conductive layer located on one or both of the opposing planar sides of the non-conductive layer. In embodiments of the electrosurgery blade assemblies having argon beam capability, the electrosurgery blade assembly includes a non-conductive tube member having a hollow tubular shaped opening and a slot where at least a portion of the conductive layer of the electrosurgery blade is positioned within the slot of the non-conductive tube member.

11 Claims, 6 Drawing Sheets

(56) References Cited

U.S. PATENT DOCUMENTS

| | | | |
|---|---|---|---|
| 5,242,442 A * | 9/1993 | Hirschfeld | A61B 18/1402 604/35 |
| 2001/0023348 A1 * | 9/2001 | Ashley | A61B 17/1671 606/41 |
| 2006/0025757 A1 | 2/2006 | Heim | |
| 2006/0264928 A1 * | 11/2006 | Kornerup | A61B 18/1402 606/45 |
| 2007/0191759 A1 * | 8/2007 | Stoller | A61B 1/3132 604/22 |
| 2008/0058801 A1 * | 3/2008 | Taylor | A61B 18/042 606/45 |
| 2011/0190768 A1 * | 8/2011 | Shvetsov | A61B 18/18 606/48 |
| 2011/0224669 A1 * | 9/2011 | Podany | A61B 18/1233 606/48 |
| 2015/0257817 A1 | 9/2015 | Zoran et al. | |

* cited by examiner

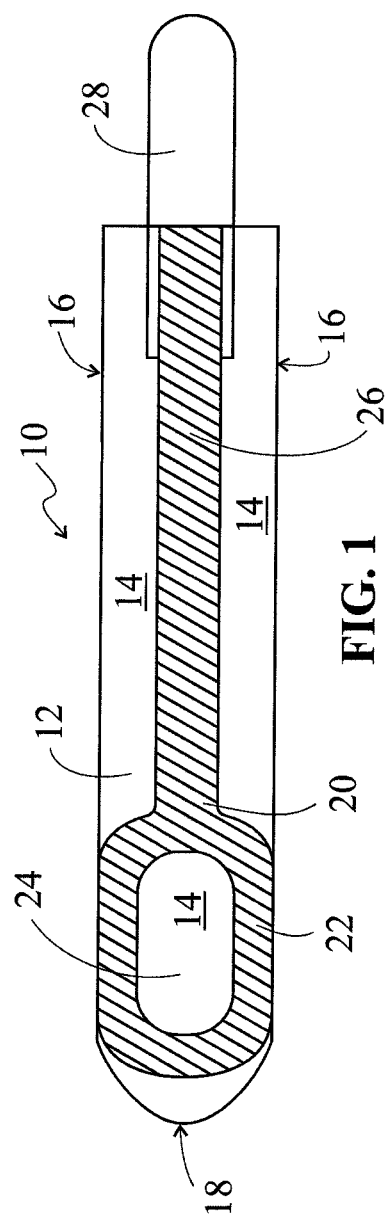
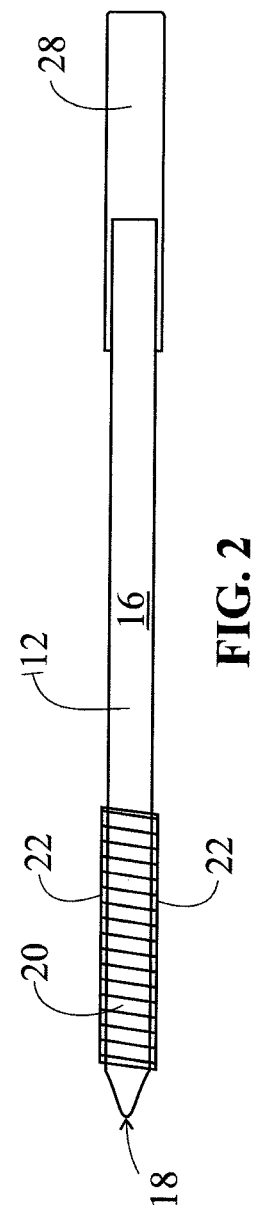
FIG. 1
FIG. 2

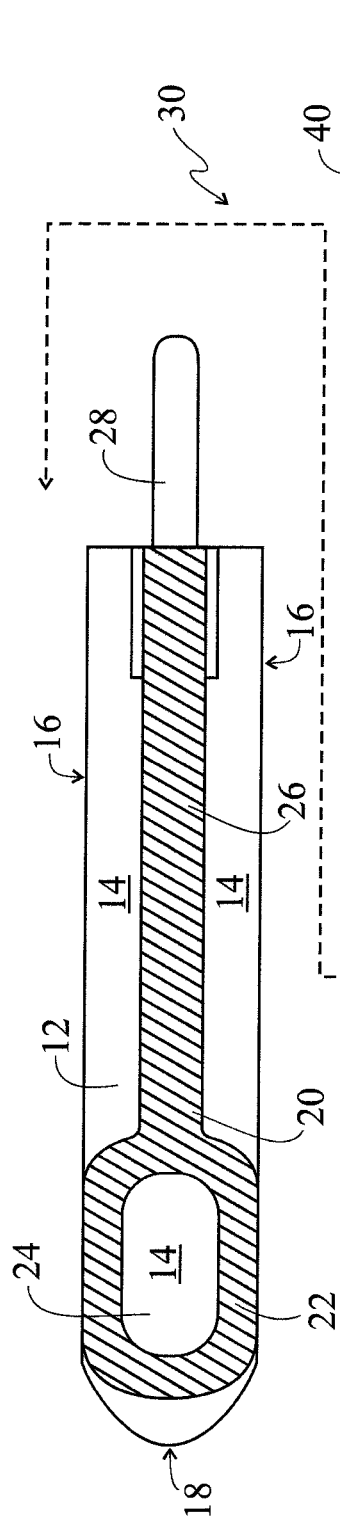
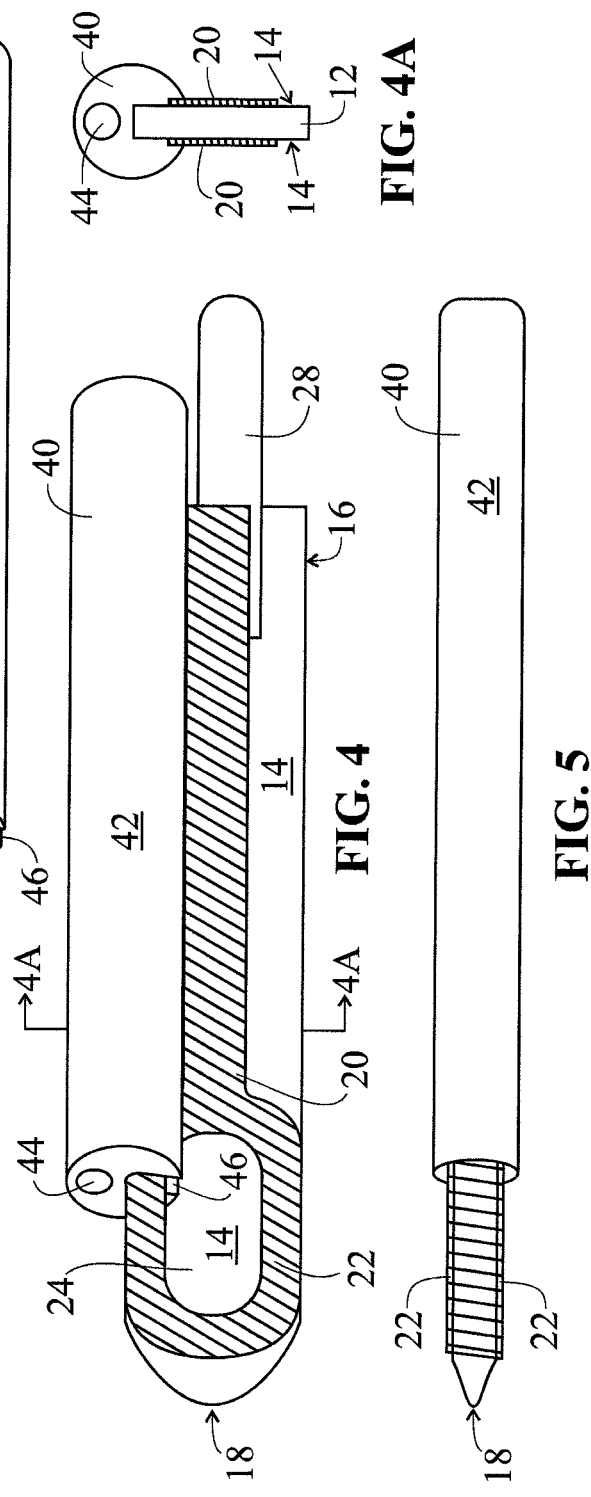

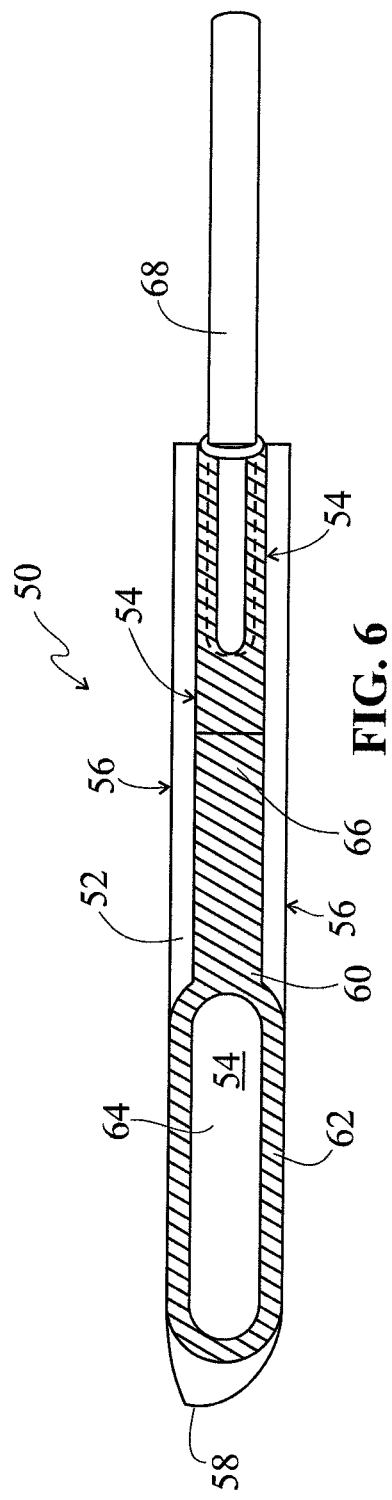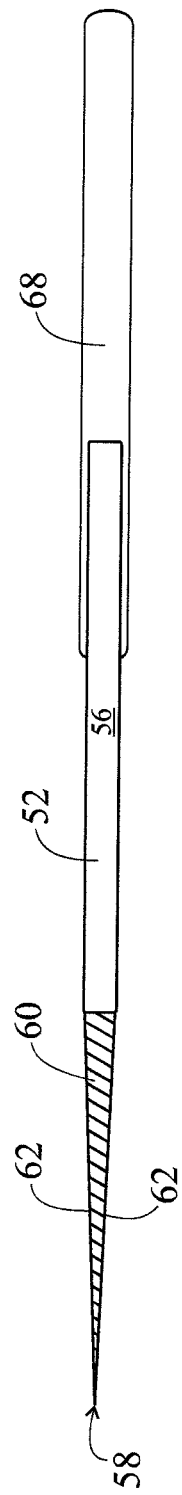
FIG. 6
FIG. 7

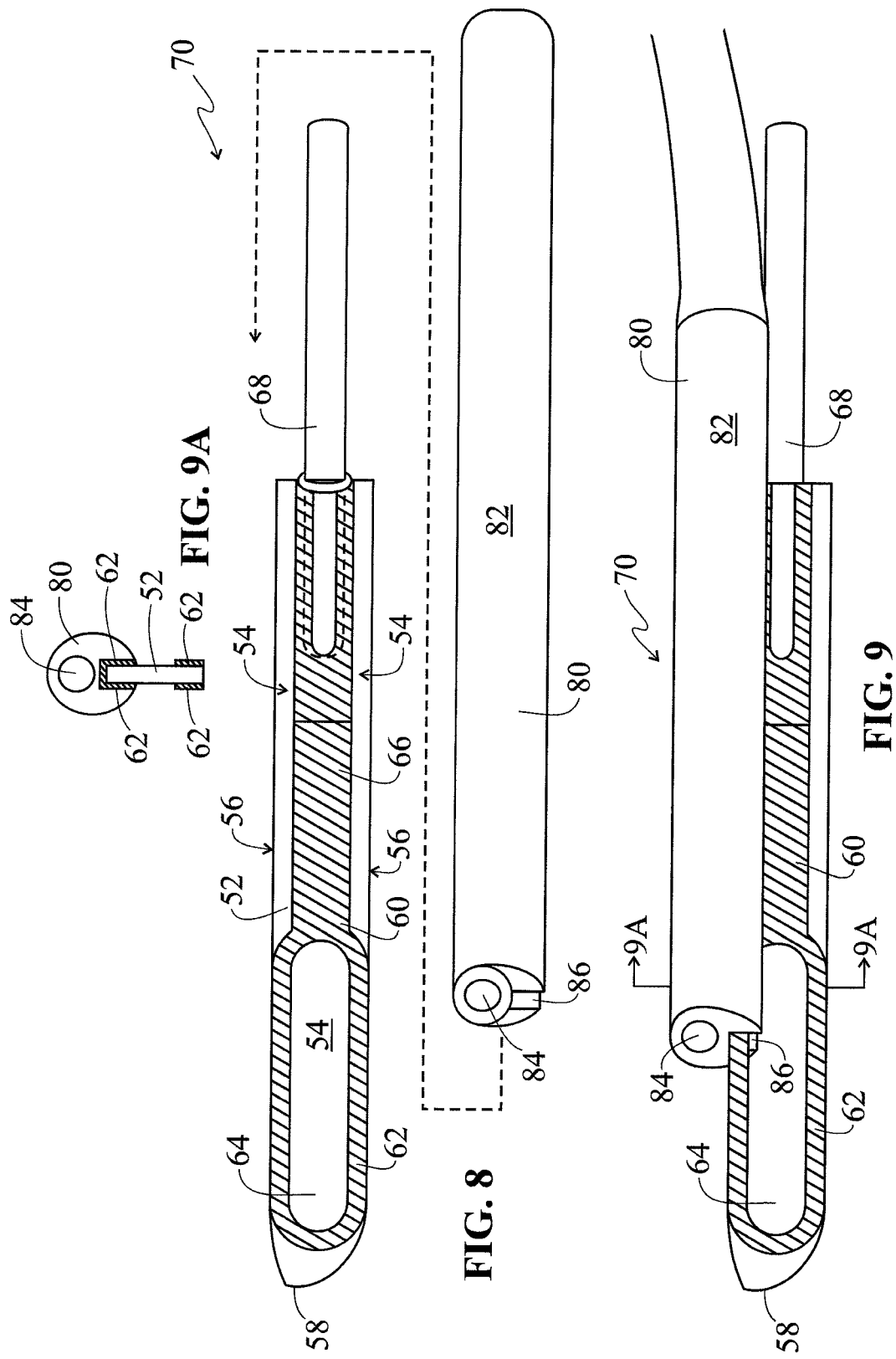

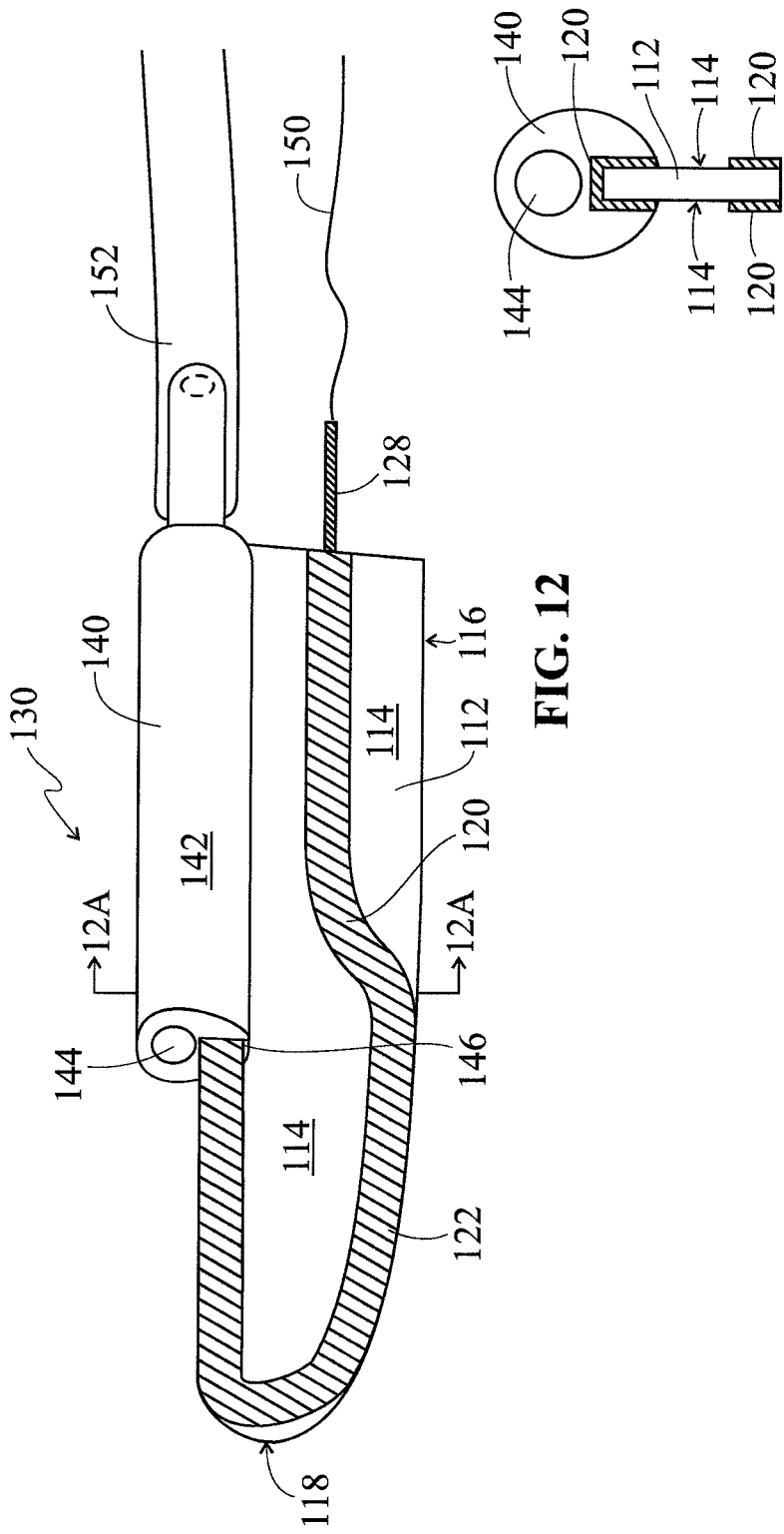

ELECTROSURGERY BLADE AND ELECTROSURGERY BLADE ASSEMBLY

FIELD OF INVENTION

The present invention is generally directed to electrosurgery blades including electrosurgery blades having argon beam capability. More particularly, the present invention relates to a monopolar electrosurgery blade which includes a non-conductive planar member having opposite planar sides and a sharp cutting tip, and a conductive layer located on one or both of the opposing planar sides of the non-conductive layer where the conductive layer lies adjacent to at least one edge of an opposing planar side of the non-conductive planar member without covering the cutting tip. In one exemplary embodiment of the electrosurgery blade, the non-conductive layer may form a closed loop shaped portion having an open interior through which the non-conductive opposing planar side is exposed. The present invention also relates to an electrosurgery blade assembly which includes the previously described monopolar electrosurgery blade plus a non-conductive tube member having a hollow tubular shaped opening, through which an inert gas can be supplied, and a slot which can be positioned over a portion of the electrosurgery blade. At least a portion of the conductive layer of the electrosurgery blade is positioned within the slot of the non-conductive tube member such that the hollow tubular shaped opening of the non-conductive tube member is positioned so that an inert gas supplied through the hollow tubular shaped opening will come in contact with at least a portion of the conductive layer of the electrosurgery blade thereby creating an ionized gas.

BACKGROUND OF THE INVENTION

Typical electrosurgical pencils use an electrode blade which functions as an active electrode for use in performing cutting and coagulation during electrosurgery and a return electrode usually comprising an adhesive for attachment to a patient's skin. When the electrosurgery pencil is activated, the RF energy circulates from the active electrode to the return electrode through the patient's body with the distance between the active and return electrodes being fairly significant. Electrosurgery uses a RF generator and handpiece with an electrode to provide high frequency, alternating radio frequency (RF) current input at various voltages (2000-10,000V) depending on the function, namely coagulation vs. cutting. For cutting, heat generated from continuous RF high voltage conduction can create a vapor pocket which vaporizes and explodes a small section of tissue cells which results in an incision. Because of the heat generated, the lateral damage to the tissue is great and the possible necrosis of the tissue is high. For coagulation, voltage is usually lower than in cut mode and the slower heating process results in less heat. As a result, no vapor pocket is formed so the tissue for the most part remains intact but with cells and vessels destroyed and sealed at the point of contact.

It is also common to use argon beam coagulators during electrosurgery. In argon beam coagulation (ABC), plasma is applied to tissue by a directed beam of ionized argon gas (plasma) which causes a uniform and shallow coagulation surface thereby stopping blood loss. However, argon beam enhanced cutting may also be performed using application of an ionized argon gas.

At present, electrosurgery is often the best method for cutting and argon beam coagulation is often the best method for cessation of bleeding during surgery. Surgeons typically need to switch between argon beam coagulation and electrosurgery modes depending on what is happening during the surgery and what they need to achieve at a particular point in the surgery such as cutting, or making incisions in tissue, or stopping the bleeding at the surgical site.

However, since surgical tools and devices currently available to surgeons require switching between these two methods during the surgical procedure, there is a need for a surgical device or tool that enables a surgeon or user to utilize the best methods used for cutting and cessation of bleeding at the surgical site at the same time, or simultaneously, in addition to being able to use them separately. An electrosurgery blade having a sharp edge for cutting and RF and argon beam capability for capsulation would meet this need. The electrosurgery blades with a sharp edge and argon beam capability described with reference to the present invention could be used with an electrosurgery handpiece/pencil that does not have smoke evacuation capability but are also intended to be used with an electrosurgery handpiece/pencil that is capable of smoke evacuation during the electrosurgery procedure.

Such a surgical device or tool would enable the surgeon or user to increase both the efficiency and accuracy of the surgery by enabling the surgeon or user to perform both tissue cutting and coagulation at the same time without switching between modes or methods thereby decreasing operating time and reducing or eliminating the lateral damage to the tissue. In addition, performing both tissue cutting and coagulation at the same time along with smoke evacuation would protect the surgeon and staff form inhaling smoke and particles and also enable the surgeon or user to more clearly view the surgical site to ensure accuracy during the procedure without the need to stop and switch modes in order to stop bleeding at the surgery site before being able to clearly see the surgical site.

SUMMARY OF THE INVENTION

The present invention is directed to an electrosurgery blade for use with an electrosurgery handpiece/pencil with smoke evacuation, or an electrosurgery handpiece/pencil without smoke evacuation, that includes a non-conductive planar member having opposite planar sides with opposing elongated edges and a sharp cutting tip, and a conductive layer located on one or both opposing planar sides where the conductive layer lies adjacent to at least one of the opposing edges of the non-conductive planar member without covering the cutting tip. More specifically, at least a portion of the one or more opposing planar sides of the non-conductive planar member is exposed near an end of the sharp cutting tip and is not covered by the conductive layer. In one exemplary embodiment, the conductive layer may form a closed loop shaped portion having an open interior through which the non-conductive opposing planar side is exposed. The conductive layer may further comprise a rectangular shaped portion extending from the closed loop shaped portion of the conductive layer.

The non-conductive planar member may comprise an inorganic, non-metallic solid material, such as a ceramic, for example. The conductive layer may comprise one or more materials such as, for example, stainless steel, copper, silver, gold, and/or titanium.

In another exemplary embodiment, there is a conductive layer that forms a closed loop shaped portion located on each of the non-conductive opposite planar sides of the planar member where each of the closed loop shaped portions of the conductive layer extend to the opposing elongated edges of each respective opposite planar side. In yet another exemplary embodiment, the conductive layer covers a portion of the opposing elongated edges of each of the opposite planar sides such that it joins the closed loop portions located on each of the opposite planar sides. In still another exemplary embodiment, the conductive layer may be present on only one of the non-conductive opposite planar sides such that it also extends over the top edge of the non-conductive planar member. In yet another exemplary embodiment, the electrosurgery blade may further comprise a shaft in communication with an end of a rectangular shaped portion of the conductive layer located opposite the closed loop portion(s) of the conductive layer where the shaft is capable of being connected to an electrosurgery pencil.

The present invention is also directed to an electrosurgery blade assembly which includes the previous described exemplary embodiments of the electrosurgery blade plus a non-conductive tube member having a hollow tubular shaped opening contained therein, through which an inert gas can be supplied, and a slot which can be positioned over a portion of the electrosurgery blade. At least a portion of the conductive layer of the electrosurgery blade is positioned within the slot of the non-conductive tube member such that the hollow tubular shaped opening of the non-conductive tube member is positioned so that an inert gas supplied through the hollow tubular shaped opening will come in contact with at least a portion of the conductive layer of the electrosurgery blade thereby creating an ionized gas. Like the non-conductive planar member, the non-conductive tube member may comprise an inorganic, non-metallic solid material, such as a ceramic, for example.

BRIEF DESCRIPTION OF THE DRAWINGS

The subject invention will hereinafter be described in conjunction with the appended drawing figures, wherein like numerals denote like elements, and FIG. 1 is a side view of a first exemplary embodiment of the electrosurgery blade of the present invention;

FIG. 2 is a top view of the exemplary embodiment of the electrosurgery blade shown in FIG. 1;

FIG. 3 is a schematic showing an exemplary embodiment of an electrosurgery blade assembly of the present invention which shows an exploded view of the positioning of a non-conductive tube member over the exemplary embodiment of the electrosurgery blade shown in FIG. 1 to provide the electrosurgery blade shown in FIG. 1 with argon beam capability;

FIG. 4 is a side perspective view of the exemplary embodiment of the electrosurgery blade assembly of the present invention depicted in FIG. 3;

FIG. 4A is a cross-sectional view taken along line 4A-4A of FIG. 4;

FIG. 5 is a top perspective view of the exemplary embodiment of the electrosurgery blade assembly of the present invention shown in FIGS. 3 and 4;

FIG. 6 is a side view of another exemplary embodiment of the electrosurgery blade of the present invention;

FIG. 7 is a top view of the exemplary embodiment of the electrosurgery blade shown in FIG. 6;

FIG. 8 is a schematic showing another exemplary embodiment of an electrosurgery blade assembly of the present invention which shows an exploded view of the positioning of a non-conductive tube member over the exemplary embodiment of the electrosurgery blade shown in FIG. 6 to provide the electrosurgery blade shown in FIG. 6 with argon beam capability;

FIG. 9 is a side perspective view of the exemplary embodiment of the electrosurgery blade assembly of the present invention depicted in FIG. 8;

FIG. 9A is a cross-sectional view taken along line 9A-9A of FIG. 9;

FIG. 12 is a side perspective view of still another exemplary embodiment of the electrosurgery blade assembly of the present invention having a non-conductive tube member positioned over a portion of the exemplary embodiment of the electrosurgery blade shown in FIG. 10; and FIG. 12A is a cross-sectional view taken along line 12A-12A of FIG. 12.

DETAILED DESCRIPTION OF EXEMPLARY EMBODIMENTS

Figure 10:
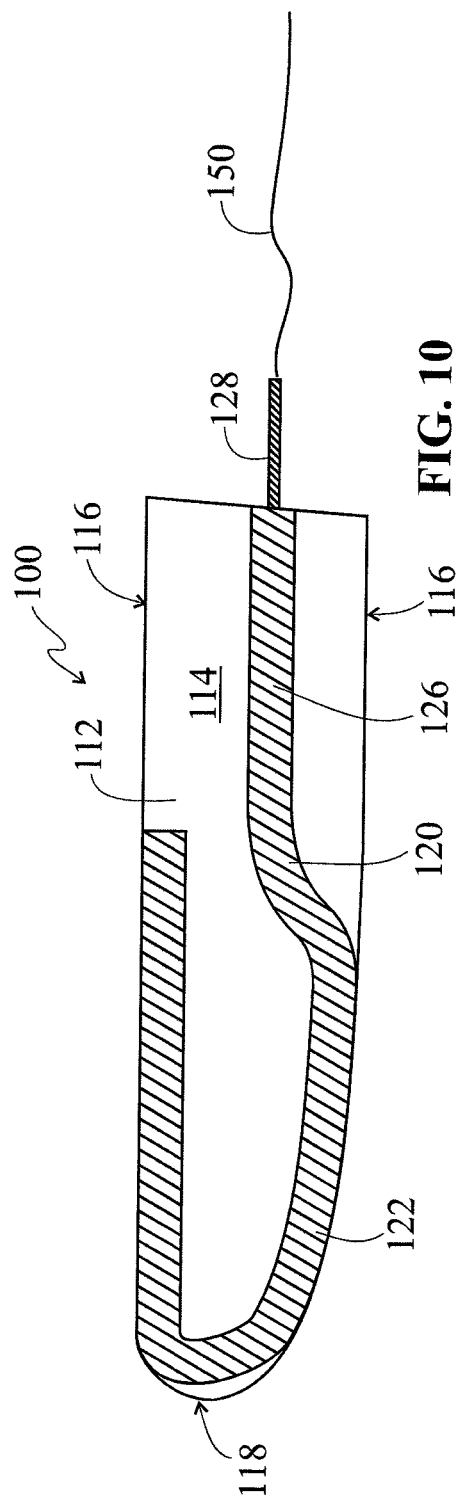
FIG. 10 is a side view of still another exemplary embodiment of the electrosurgery blade of the present invention.
Figure 11:
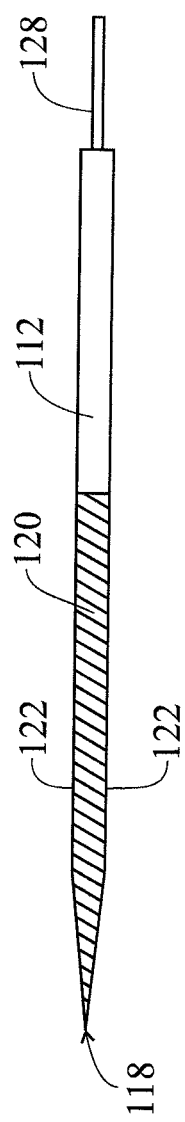
FIG. 11 is a top view of the exemplary embodiment of the electrosurgery blade shown in FIG. 10.

The exemplary embodiments of the electrosurgery blade of the present invention enable a user or surgeon to use an electrosurgery blade having a non-conductive planar member with opposite planar sides and a sharp cutting edge, and a conductive layer located on one or both of the opposing sides, for cutting and/or coagulation. Exemplary embodiments of the electrosurgery blade assembly of the present invention include the exemplary embodiments of the electrosurgery blade of the present invention plus a non-conductive tube member having a hollow tubular shaped opening and a slot with at least a portion of the conductive layer of the electrosurgery blade positioned within the slot to enable a user or surgeon to separately use a sharp edged electrode for cutting and/or coagulation, separately use an argon beam for cutting and/or coagulation, or simultaneously use a sharp edged electrode and an argon beam for cutting and/or coagulation.

FIG. 1 shows a side view of a first exemplary embodiment of the electrosurgery blade 10 of the present invention having a non-conductive planar member 12 with opposite planar sides 14 having opposing elongated edges 16 and a sharp cutting tip 18, and a conductive layer 20 located on one or both opposing planar sides 14 where each conductive layer 20 includes a loop shaped portion 22 having an open interior 24 through which the opposing planar side 14 of the non-conductive planar member 12 is exposed. The conductive layer 20 is configured such that it leaves a portion of one or both opposing planar sides 14 of non-conductive planar member 12 exposed near the sharp cutting tip 18 of non-conductive planar member 12. The conductive layer 20 also includes a rectangular shaped portion 26 extending from the loop shaped portion 22 of the conductive layer 20. A shaft 28 is connected to, or in communication with, the rectangular shaped portion 26 of the conductive layer 20 near an end of the rectangular shaped portion 26 that is opposite the loop shaped portion 22 of the conductive layer 20. The shaft 28 of electrosurgery blade 10 may be connected to an active conductor contained within an electrosurgery pencil.

The non-conductive planar member 12 may comprise an inorganic, non-metallic solid material, such as a ceramic, for example, and the conductive layer 20 may comprise one or more materials such as, for example, stainless steel, copper, silver, gold, and/or titanium. The shaft 28 may comprise a metal or other conductive material that is covered by a sheath of non-conductive material.

A top view of the exemplary embodiment of the electrosurgery blade depicted in FIG. 1 is shown in FIG. 2. As shown in FIG. 2, this exemplary embodiment of the electrosurgery blade 10 of the present invention includes a conductive layer 20 having a loop shaped portion 22 that extends up and over the opposing elongated edges 16 of each respective opposite planar side 14 thereby providing a conductive layer over a top of the non-conductive planar member 12.

FIG. 3 is a schematic showing an exemplary embodiment of the electrosurgery blade assembly 30 of the present invention which shows an exploded view of the positioning of a non-conductive tube member 40 over the exemplary embodiment of the electrosurgery blade 10 shown in FIG. 1 to provide the electrosurgery blade 10 shown in FIG. 1 with argon beam capability. Non-conductive tube member 40 includes an outer surface 42, a hollow tubular shaped opening 44, and a slot 46 into which electrosurgery blade 10 is placed so that at least a portion of opposing planar sides 14 and at least a portion of conductive layer 20 of electrosurgery blade 10 are positioned within the slot 46 of non-conductive tube member 40. Further, the electrosurgery blade 10 is located within slot 46 so that the hollow tubular shaped opening 44 is positioned such that an inert gas supplied through hollow tubular shaped opening 44 will come into contact with at least a portion of conductive layer 20 of electrosurgery blade 10 thereby creating an ionized gas (plasma). A side perspective view of the exemplary embodiment of the electrosurgery blade assembly 30 of the present invention depicted in FIG. 3 is shown in FIG. 4 and a cross-sectional view of the electrosurgery blade assembly 30 taken along line 4A-4A of FIG. 4 is shown in FIG. 4A. As can be seen in FIGS. 4 and 4A, the hollow tubular shaped opening 44 of non-conductive tube member 40 enables an inert gas, such as argon gas, to pass through non-conductive tube member 40 and over at least a portion of the conductive layer 20 to create an ionized gas (plasma). The ionized gas (plasma) is created when the electrode comes into contact with the body/patient thereby creating a closed circuit with a return electrode attached to the body/patient which enables argon beam cutting and/or coagulation with the electrosurgery blade 30.

FIG. 5 is a top perspective view of the exemplary embodiment of the electrosurgery blade assembly of the present invention shown in FIGS. 3 and 4. As previously described above, a source of inert argon gas can be supplied through hollow tubular shaped opening 44 of non-conductive tube member 40 thereby enabling a user or surgeon to use the electrosurgery blade assembly 30 shown in FIGS. 3-5 to perform cutting and/or coagulation separately with the combination of the non-conductive planar member and conductive layer, cutting and/or coagulation separately using an argon beam, or cutting and/or coagulation while simultaneously using the combination of the non-conductive planar member and conductive layer with the argon beam.

FIG. 6 is a side view of still another exemplary embodiment of the electrosurgery blade 50 of the present invention having a non-conductive planar member 52 with opposite planar sides 54 having opposing elongated edges 56 and a sharp cutting tip 58, and a conductive layer 60 located on one or both opposing planar sides 54 where each conductive layer 60 includes an elongated loop shaped portion 62 having an open interior 64 through which the opposite planar side 54 of the non-conductive planar member 52 is exposed. The conductive layer 60 is configured such that it leaves at least a portion of one or both opposing planar sides 54 of non-conductive planar member 52 exposed near the sharp cutting tip 58 of the non-conductive planar member 52. The conductive layer 60 also includes a rectangular shaped portion 66 extending from the elongated loop shaped portion 62 of the conductive layer 60. A shaft 68 is connected to, or in communication with, the rectangular shaped portion 66 of the conductive layer 60 near an end of the rectangular shaped portion 66 that is opposite the elongated loop shaped portion 62 of the conductive layer 60. The shaft 68 of electrosurgery blade 50 may be connected to an active conductor contained within an electrosurgery pencil.

The non-conductive planar member 52 may comprise an inorganic, non-metallic solid material, such as a ceramic, for example, and the conductive layer 60 may comprise one or more materials such as stainless steel, copper, silver, gold, and/or titanium. The shaft 68 may comprise a metal or other conductive material that is covered by a sheath of non-conductive material.

A top view of the exemplary embodiment of the electrosurgery blade 50 depicted in FIG. 6 is shown in FIG. 7. As shown in FIG. 7, this exemplary embodiment of the electrosurgery blade 50 of the present invention includes a conductive layer 60 on each opposite planar side 54 of non-conductive planar member 52 having an elongated loop shaped portion 62 that extends to, and covers, the opposing elongated edges 56 of each respective opposite planar side 54 thereby joining and connecting the elongated closed loop portions 62 of the conductive layer 60 located on each of the opposite planar sides 54 of the non-conductive planar member 52.

FIG. 8 is a schematic showing another exemplary embodiment of the electrosurgery blade assembly 70 of the present invention which shows an exploded view of the positioning of a non-conductive tube member 80 over the exemplary embodiment of the electrosurgery blade 50 shown in FIG. 6 to provide the electrosurgery blade 50 shown in FIG. 6 with argon beam capability. Non-conductive tube member 80 includes an outer surface 82, a hollow tubular shaped opening 84, and a slot 86 into which electrosurgery blade 50 is placed so that at least a portion of opposing planar side 54 and at least a portion of conductive layer 60 of electrosurgery blade 50 is positioned within slot 86 of non-conductive tube member 80. A side perspective view of the exemplary embodiment of the electrosurgery blade assembly 70 of the present invention depicted in FIG. 8 is shown in FIG. 9 and a cross-sectional view of the electrosurgery blade assembly 70 taken along line 9A-9A of FIG. 9 is shown in FIG. 9A. As can be seen in FIGS. 9 and 9A, the hollow tubular shaped opening 84 of non-conductive tube member 80 enables an inert gas, such as argon gas, to pass through non-conductive tube member 80 and over at least a portion of the conductive layer 62 to create an ionized gas (plasma) when the electrode comes into contact with the body/patient thereby creating a closed circuit with a return electrode attached to the body/patient which enables argon beam cutting and/or coagulation with the electrosurgery blade 70.

As previously described with reference to the exemplary embodiment of the electrosurgery blade 30 show in in FIGS. 3-5, a source of argon gas can be provided through hollow tubular shaped opening 84 of non-conductive tube member 80 thereby enabling a user or surgeon to use the electrosurgery blade 70 show in FIGS. 8-9 to perform cutting and/or coagulation separately with the combination of the non-conductive planar member and conductive layer, cutting and/or coagulation separately using an argon beam, or cutting and/or coagulation while simultaneously using the combination of the non-conductive planar member and conductive layer with the argon beam.

FIG. 10 shows a side view of a still another exemplary embodiment of the electrosurgery blade 100 of the present invention having a non-conductive planar member 112 with opposite planar sides 114 having opposing elongated edges 116 and a sharp cutting tip 118, and a conductive layer 120 located on one or both opposing planar sides 114 where each conductive layer 120 includes a hook shaped portion 122. The conductive layer 120 is configured such that at least a portion of one or both opposing planar sides 114 of non-conductive planar member 112 are exposed near the sharp cutting tip 118 of non-conductive planar member 112. The conductive layer 120 also includes a rectangular shaped portion 126 extending from the hook shaped portion 122 of the conductive layer 120. A metal contact 128 is connected to, or in communication with, the rectangular shaped portion 126 of the conductive layer 120 near an end of the rectangular shaped portion 126 that is opposite the hook shaped portion 122 of the conductive layer 120. The metal contact 128 of electrosurgery blade 110 may be connected to an electrosurgery pencil via a conductive wire 150 or similar type of conductive contact or medium contained within the electrosurgery pencil.

The non-conductive planar member 112 may comprise an inorganic, non-metallic solid material, such as a ceramic, for example, and the conductive layer 120 may comprise one or more materials such as, for example, stainless steel, copper, silver, gold, and/or titanium. The metal contact 128 may comprise a metal that is covered by a sheath of non-conductive material.

A top view of the exemplary embodiment of the electrosurgery blade 100 depicted in FIG. 10 is shown in FIG. 12. As shown in FIG. 12, this exemplary embodiment of the electrosurgery blade 100 of the present invention includes a conductive layer 120 that extends up and over the opposing elongated edges 116 of each respective opposite planar side 114 thereby providing a conductive layer over a top of the non-conductive planar member 112.

FIG. 12 shows a side perspective view of still another exemplary embodiment of the electrosurgery blade assembly 130 of the present invention having a non-conductive tube member 140 positioned over a portion of the exemplary embodiment of the electrosurgery blade 100 shown in FIG. 10 to provide the electrosurgery blade 100 shown in FIG. 10 with argon beam capability. Non-conductive tube member 140 includes an outer surface 142, a hollow tubular shaped opening 144, and a slot 146 into which electrosurgery blade 100 is placed so that at least a portion of opposing planar sides 114 and at least a portion of conductive layer 120 of electrosurgery blade 100 are positioned within the slot 146 of non-conductive tube member 140. Further, the electrosurgery blade 100 is located within slot 146 so that the hollow tubular shaped opening 144 is positioned such that an inert gas supplied through hollow tubular shaped opening 144 will come into contact with at least a portion of conductive layer 120 of electrosurgery blade 100 thereby creating an ionized gas (plasma). The end of non-conductive tube member 140 located opposite the end of non-conductive tube member 140 located closest to sharp cutting tip 118 of electrosurgery blade 100 is connected to a tube 152, which supplies an inert gas such as argon gas, that may be contained within, or comprise part of, an electrosurgery pencil. A cross-sectional view of the electrosurgery blade assembly 130 taken along line 12A-12A of FIG. 12 is shown in FIG. 12A. As can be seen in FIGS. 12 and 12A, the hollow tubular shaped opening 144 of non-conductive tube member 140 enables an inert gas, such as argon gas, to pass through non-conductive tube member 140 and over at least a portion of the conductive layer 120 to create an ionized gas (plasma) when the electrode comes into contact with the body/patient thereby creating a closed circuit with a return electrode attached to the body/patient which enables argon beam cutting and/or coagulation with the electrosurgery blade 130.

The detailed description of exemplary embodiments of the invention herein shows various exemplary embodiments of the invention. These exemplary embodiments and modes are described in sufficient detail to enable those skilled in the art to practice the invention and are not intended to limit the scope, applicability, or configuration of the invention in any way. Rather, the following disclosure is intended to teach both the implementation of the exemplary embodiments and modes and any equivalent modes or embodiments that are known or obvious to those reasonably skilled in the art. Additionally, all included examples are non-limiting illustrations of the exemplary embodiments and modes, which similarly avail themselves to any equivalent modes or embodiments that are known or obvious to those reasonably skilled in the art.

Other combinations and/or modifications of structures, arrangements, applications, proportions, elements, materials, or components used in the practice of the instant invention, in addition to those not specifically recited, can be varied or otherwise particularly adapted to specific environments, manufacturing specifications, design parameters, or other operating requirements without departing from the scope of the instant invention and are intended to be included in this disclosure.

Unless specifically noted, it is the Applicant's intent that the words and phrases in the specification and the claims be given the commonly accepted generic meaning or an ordinary and accustomed meaning used by those of ordinary skill in the applicable arts. In the instance where these meanings differ, the words and phrases in the specification and the claims should be given the broadest possible, generic meaning. If any other special meaning is intended for any word or phrase, the specification will clearly state and define the special meaning.

The invention claimed is:

1. An electrosurgery blade assembly comprising:
a non-conductive planar member having opposite planar sides with opposing elongated edges and a cutting tip;
a conductive layer located on at least one side of the opposite planar sides wherein the conductive layer lies adjacent to at least one of the opposing elongated edges of the non-conductive planar member; and
a non-conductive tube member having a hollow tubular shaped opening contained therein and a slot contained therein wherein the slot is positioned over at least a portion of the conductive layer such that the slot is in physical contact with the conductive layer.

2. The electrosurgery blade assembly of claim 1 wherein the slot of the non-conductive tube member is also positioned over at least a portion of the non-conductive planar member.

3. The electrosurgery blade assembly of claim 1 wherein the non-conductive tube member comprises a ceramic.

4. The electrosurgery blade assembly of claim 1 wherein at least a portion of an outer surface of the non-conductive tube member is located on each of the opposite planar sides of the non-conductive planar member.

5. The electrosurgery blade assembly of claim 4 wherein the hollow tubular shaped opening of the non-conductive tube member is positioned such that an inert gas supplied through the hollow tubular shaped opening will come in contact with at least a portion of the conductive layer.

6. The electrosurgery blade assembly of claim 1 wherein said non-conductive planar member comprises a ceramic.

7. The electrosurgery blade assembly of claim 1 wherein the conductive layer comprises at least one of a stainless steel, a copper, a gold, a silver, and a titanium.

8. The electrosurgery blade assembly of claim 1 wherein the conductive layer forms a closed loop shaped portion located on one or more of the opposite planar sides of the non-conductive planar member.

9. The electrosurgery blade assembly of claim 8 wherein the conductive layer is on both opposite planar sides of the non-conductive planar member and covers a portion of the opposing elongated edges located on a top of each of the opposite planar sides such that it joins the elongated closed loop portions located on each of the opposite planar sides.

10. The electrosurgery blade assembly of claim 8 wherein at least a portion of an outer surface of the non-conductive tube member is located on each of the opposite planar sides of the non-conductive planar member.

11. The electrosurgery blade assembly of claim 10 wherein the hollow tubular shaped opening of the non-conductive tube member is positioned such that an inert gas supplied through the hollow tubular shaped opening will come in contact with at least a portion of the conductive layer of the electrosurgery blade.

* * * * *